United States Patent [19]

Mortensen

[11] 4,385,590
[45] May 31, 1983

[54] APPARATUS FOR ON-SITE DETECTION OF MASTITIS IN MILK ANIMALS

[76] Inventor: Bruce Mortensen, Rte. 3, Rupert, Id. 83350

[21] Appl. No.: 329,645

[22] Filed: Dec. 11, 1981

[51] Int. Cl.³ .............................................. A01J 7/00
[52] U.S. Cl. ............................. 119/14.01; 119/14.14; 119/14.54
[58] Field of Search ............... 119/14.01, 14.08, 14.14, 119/14.54, 14.55

[56] References Cited

U.S. PATENT DOCUMENTS

| | | | |
|---|---|---|---|
| 2,518,831 | 8/1950 | Stalloch et al. | 119/14.01 X |
| 3,125,067 | 3/1964 | Fosnes | 119/14.55 |
| 3,150,637 | 9/1964 | Fosnes | 119/14.54 |
| 3,406,663 | 10/1968 | Duncan | 119/14.01 |
| 4,190,020 | 2/1980 | Tamas et al. | 119/14.08 |

*Primary Examiner*—Hugh R. Chamblee
*Attorney, Agent, or Firm*—Lynn G. Foster

[57] ABSTRACT

A filtering cell through which milk from each cow of a herd is caused to pass for immediate detection of mastitis. Milk from the different teats of each animal is combined and passed through the filtering device which comprises a housing and a filter through which the milk passes. A light producing device is located on one side of the filter and a photoelectric cell on the other side. Thus, any decreased flow of light through the filter caused by the collection of a white clotted material from the milk infected by mastitis will be optically identified. If desired, a signal device may be used to notify the on-site operator of the existence of mastitis. The housing comprises two funnel shaped pieces which are connected to each other by a hinge. The suction of the mechanical milking machine holds the two halves together during use. A valve is closed to retrieve the suction and accommodate opening the housing via the hinge. An overflow passageway is provided in the event the filter becomes clogged. This facilitates easy removal and replacement of the filter from time to time.

14 Claims, 1 Drawing Figure

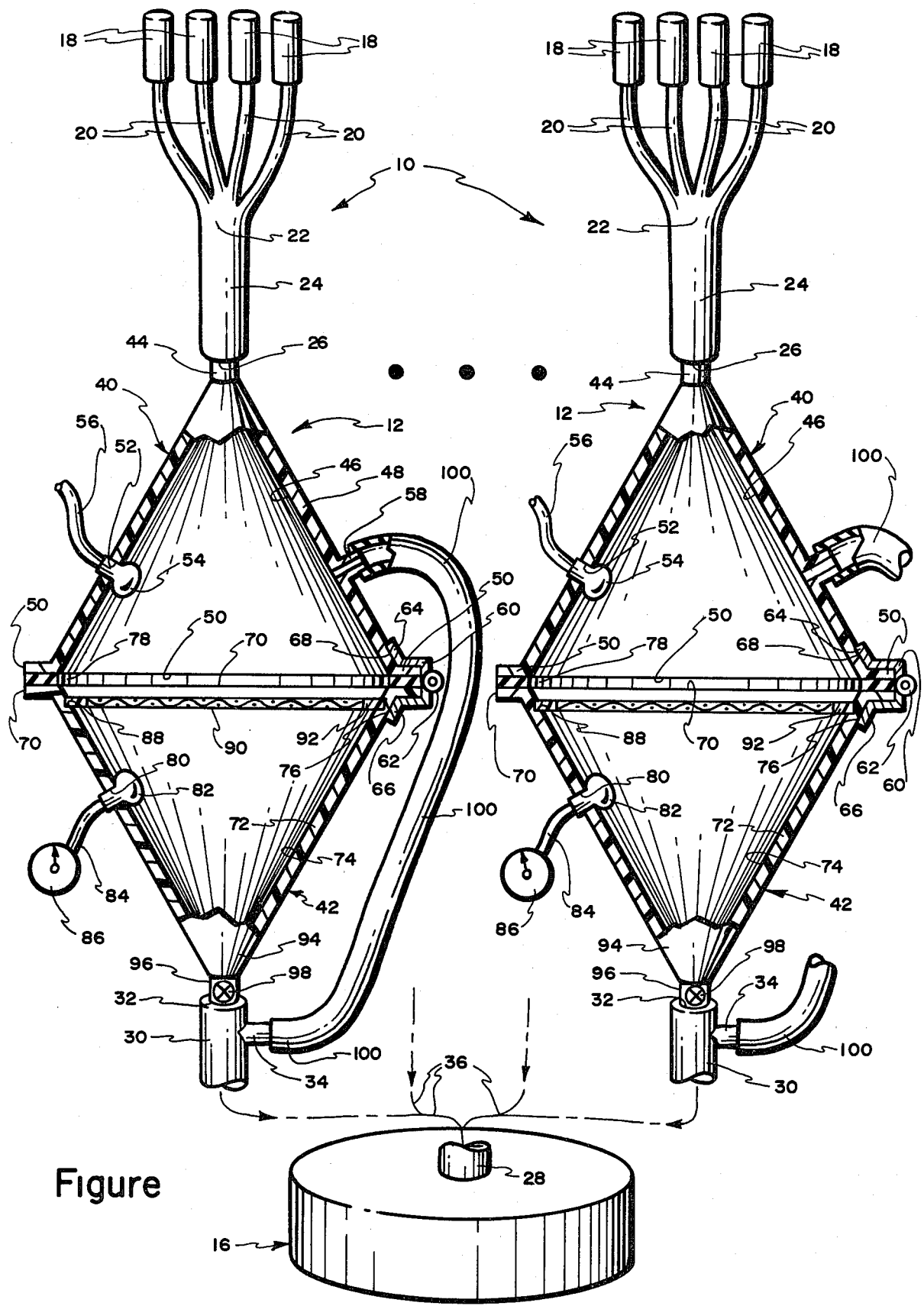
Figure

APPARATUS FOR ON-SITE DETECTION OF MASTITIS IN MILK ANIMALS

BACKGROUND

1. Field of Invention

The invention relates generally to mastitis detection and more particularly to a novel fool proof on-site mastitis detector for use in mechanized milking operations.

2. Prior Art

Mastitis is a disease of the udder, which infects milk animals such as cows, sheep, and goats and causes serious losses of milk production, the disease can also be terminal. Early detection is significant in effectuating an early cure to avoid permanent injury to the udder. Heretofore, it has been the practice of dairy farmers to send milk samples from time to time to distant laboratories for analysis to determine whether or not any cow has mastitis. This is expensive and time consuming, especially where each cow of a herd needs to be tested.

Once mastitis is advanced in a given cow, the injury to the udder is permanent as the spongy cells of the udder where the milk accumulates do not regenerate once disabled by mastitis. Many changes in the characteristics of milk occur when mastitis infects a milk animal, e.g. the chloride content of the milk, its pH, its conductivity, its opacity, its viscosity, and so on. One of the most pronounced changes in the presence in the milk of solid white particles or curdles. The cost of equipment to measure these various parameters varies widely, as does their durability, the difficulty of keeping the working parts clean and sterile, the difficulty of comprehending the indication presented, and the lack of suitability for use on-site in the farm milking operation.

Heretofore most mastitis screening has been done by periodically sending samples to a laboratory. There have however been some proposals for on-site detection. There are disclosed in U.S. Pat. Nos. 3,695,230; 3,664,306; 3,762,371 and 3,968,774. Each can be used during milking in an attempt to determine the presence of mastitis by comparing the conductivity of milk from different quarters of an udder, using an electrical bridge. Comparing resistance presents several problem.

For example, inaccurate results will be obtained if ineffective cleaning leaves coatings of fat or milk stains on the electrodes of conductivity cells forming part of the comparison apparatus. Uniting the electrodes to the surrounding molding without leaving crevices in which bacteria and solid deposits can lodge is difficult and tends to make conductivity cells with electrodes which contact the milk fairly expensive.

A further problem arises in taking conductivity measurements while the liquid flows continually through the apparatus. An additional problem associated with reliance upon measurements of change in conductivity to detect mastitis is that many other factors cause changes in conductivity, including diet, condition of the animal, season of the year, temperature of the milk, and so on.

In addition to these other problems, conductivity measuring devices have several other inherent disadvantages. They require segregation of the milk from each section of the udder of each cow until the testing process is complete. They require complicated and expensive electrical circuitry using a minimum of eight electrodes in each device. These devices also necessarily bring four currents of electricity into direct contact with the stream of milk coming from the teats, allowing the possibility of electrical shock to the animal.

BRIEF SUMMMARY AND OBJECTS OF THE INVENTION

The present invention provides a simplified mastitis detection system comprising individual filter sites, in a milking system, between each cow milking site and a central milk storage tank whereby solid white particles from a specific animal, which are indicative of mastitis, are accumulated on a filter for immediate visual or optical detection. Thus, immediate identification of the existence of the disease, the cow so infected and prompt treatment are economically facilitated without the requirement of specialized personnel or technical training, either for operation or maintenance of the system. The time delays and expense of laboratory examination are avoided as are the risks of substantial permanent damage to the udder. According to the present invention no electric current is or may be brought in contact with the milk or the animal. The mastitis is detected by segregating the white particles or matter, which indicate the presence of the disease, on a filter through which, for example, the light is beamed from a small low voltage lamp. The intensity of which is sensed on the other side of the filter by a photo electric cell. The presence of clotted material on the filter decreases the light intensity passing through the filter and the photo electric cell immediately visually informs the operator that mastitis is present in a specific cow at a specific milking site. According to the present invention factors such as diet of the animal, season of the year, etc. which may give a false reading on a conductivity measuring system do not affect the accuracy of mastitis testing according to the present invention since conductivity is not the factor being measured. The present invention in its presently preferred form is manufactured from materials with a smooth surface and is designed so as to minimize if not eliminate the areas where bacteria and solids could collect. The present invention is easily cleaned by opening the device and cleaning it in the same manner as the other parts of the milking equipment. The present invention does not require that the milk from each teat be segregated prior to and during the testing process thus making it easily adaptable to standard vacuum type milking equipment which combines the streams of milk from a single animal after they leave the animal. Advantageously, the present invention is inexpensive to manufacture and is simple to install, use and maintain. This makes available even to the small dairy farmer a quick, accurate, safe and inexpensive mechanism for detecting and facilitating instant treatment of mastitis as soon as the animal contract the malady and before it damages the udder, or infects other animals in the herd.

With the foregoing in mind, it is a primary object of the present invention to provide an inexpensive, accurate, and simple apparatus for and method of detecting mastitis in milk animals, which can be readily used in both large and small dairy farm operations.

It is also an important object of the present invention to provide a mastitis detector which measures and responds only to factors which are directly indicative of the presence of the disease and which is not affected by extraneous factors.

It is a further significant object of the invention to provide a mastitis examination for each animal during every milking at all milking site, and to inform the operator as soon as mastitis appears in the animal, so that treatment can be commenced instantly before the disease spreads or causes serious damage to the infected animal.

It is a further dominant object of the present invention to provide for mastitis detection which is completely compatible with modern milking machinery; the installation of the present invention can be quickly and easily achieved without necessitating any substantial changes in existing milking equipment.

It is a further paramount object of the present invention to provide a mastitis detector which is easily maintained in a clean condition and which can be completely opened for cleaning or replacement to components.

It is a still further and no less important object of the present invention to provide a mastitis detector which does not risk bringing electric current into contact with the milk stream or with the animal, the present invention avoiding use of conductivity of the milk to detect the disease.

These and other objects and features of the present invention will be apparent from the detailed description taken with reference to the accompanying drawings.

BRIEF DESCRIPTION OF THE DRAWING

The FIGURE is a front elevational view of a presently preferred mastitis detecting system in accordance with the present invention, with parts broken away and shown in cross section for clarity of illustration.

DETAILED DESCRIPTION OF THE ILLUSTRATED EMBODIMENT

Reference is now made to the drawings wherein like numerals are used to designate like parts throughout, a presently preferred embodiment of a on-site mastitis detection system, generally designated 10, in accordance with the present invention being illustrated in the drawing.

The filter system 10 comprises a plurality of filtration units, generally designated 12. Each filtration unit 12 is interposed between one of several conventional four teat milking units, generally designated 14, and a conventional vacuum milk storage tank, generally designated 16.

Since the milking units 14 and the vacuum tank 16 together with the mechanism for generating the vacuum are conventional and well known in the art, no extensive description is needed. Suffice it to say that each milking unit 14 comprises four suction teat engaging cups 18, each of which is in liquid and vacuum communication with the interior of a flexible elastomeric hollow hose 20. The four hollow hoses 20 of each milking unit 14 merge at site 22 into a single milk and vacuum communicating hose 24. Each hose 24 has a diameter substantially larger than the diameter of any hose 20. Each hose 24 terminates at end 26.

The milk collecting vacuumized tank 16 is illustrated as having a single influent pipe 28, sized and shaped to accommodate the flow of milk from a predetermined number of milking units 14 into the tank 16. Influent conduit 28 is in vacuum and liquid communication with a plurality of flexible hoses 30, one hose 30 servicing each milking unit 14. Each hose 30 terminates at end 32 and comprises a Tee at 34. The hoses 30 are joined together at junctures located at sites 36 so that the flow from all milking units 14 is accumulated in tank 16. Of course, if more than one tank is desired for any reason, some of the milking units 14 of any system 10 could be caused to be discharged variously into any desired number of vacuumized storage tanks without departing from the present invention.

Each filtration unit 12 comprises an upper cone shaped housing, generally designated 40, and a lower oppositely directed cone shaped housing, generally designated 42. Each housing 40 and 42 may be considered as cone or funnel-shaped in their configuration and of reverse orientation, in the illustrated embodiment.

Housing 40 comprises an upper hollow influent tube 44 sized and shaped so as to accommodate being snugly press fit into the hollow interior of hose 24 at end 26. Thus, a tight press-fit relationship exists between tube 44 and hose 24 sufficient to avoid loss of vacuum and to insure flow of milk without leakage from the hose 24 into the hollow 46 of the housing 40.

Housing 40, as well as housing 42 is preferably formed of shape retaining plastic and housing 40 may be substantially transparent to accommodate visual inspection of the interior thereof through the sloped thin wall 48 of the housing 40.

The lower end of the funnel-shaped housing 40 terminates in a radially directed annular horizontal flange 50, the wall 48 comprising an aperture 52 into which a portion of a light source 54 is integrally secured as by use of a suitable bonding agent in air tight relation to thereby preserve the vacuum within and avoid milk leakage from the interior 46 of the housing 40. The light source 54 is preferably serviced conventionally with low voltage electricity via electrical cord 56.

The wall 48 of the housing 40 also comprises an outwardly directed annulus or boss 58, which comprises a milk overflow port. The overflow port 58 functions in a manner hereinafter explained.

The upper housing 40 is joined pivotally to the lower housing 42 by a single hinge 60. More specifically, hinge 60 comprises a pivot rod 62 comprising the axis of rotation for the hinge comprising upper and lower flanges 64 and 66. Hinge 64 is secured at site 68 to the exterior surface of the housing 40 by a suitable bonding agent. Thus, the upper housing 40 together with hoses 24 and 20 may under some conditions be pivoted clockwise as viewed in the FIGURE to provide access to the interior 46 of housing 40.

The lower housing 42 also comprises a radially extending annular horizontal flange 70 having an inside radius and outside radius substantially equal to the inside and outside radius of previously described flange 50. The housing 42 also comprises a relatively thin sloped wall 72 defining a hollow interior 74 of housing 42.

The flange 66 of hinge 60 is integrally united at site 76 to the exterior surface of the wall 72 by a suitable bonding agent. The hinge 60 is sized and shaped so that flanges 50 and 70 are caused to be spaced from each other in their closed position by an essentially uniform predetermined distance. An elastomeric annular compressable seal 78 is tightly interposed between the opposed surfaces of the flanges 50 and 70 in air tight relation when in the position of the FIGURE. The annular seal 78 may be secured by a suitable adhesive or the like to one or the other of the two flanges 50 and 70.

Once the housings 40 and 42 are placed in the closed position as illustrated in the FIGURE, the vacuum within the hollow interior of the vacuum milking system will increase the sealing force in existence at seal 78 so that inadvertent opening of any filtration unit 12 is avoided.

Wall 72 of housing 42 comprises an aperture 80 in which is situated a photocell 82. An electrical cord 84 containing conductors unites the photocell 82 with a gauge 86. The housing wall 72 comprises a horizontally oriented shoulder 88 on which the rim 92 of a disc shaped filter 90 rests by force of gravity. Filter 90 comprises a material pervious to milk but impervious to mastitis particles. Filter 90 is removable, disposable and replaceable. Thus, when a new filter is needed it may be rapidly manually inserted upon manual removal of the spent filter.

Housing 42 merges at site 90 with an effluent hollow tube 96 containing an on/off valve 98. Valve 98 may be manually opened and closed. When closed, the housings 40 and 42 may be opened by rotating one in respect to the other about hinge 60. This accommodates close visual inspection of the filter replacement without interrupting the operation of the other milking units 14.

When valve 98 is opened, the housings 40 and 42 are closed and the vacuum is applied to the interior of the housings 40 and 42 as well as to the interior of the associated four teat milking unit 14. Valve 98 must be below the overflow so the vacuum will not continue through the tube into the unit.

A flexible hollow bypass hose 100 is sized and shaped so as to accommodate being press fit over tub 34 and annular projection 58 so that in the event filter 90 becomes clogged by mastitis particles, influent milk from the associated milking unit 14 will be discharged into the tank 16 via hose 100, port 34 and tube 30.

In use, with the four teat-engaging receptacles 18 of any milking unit 14 secured to the animal and the housings 40 and 42 in their closed position, the vacuum system is brought into existence by valve 98 being placed in its open position so that the interior of the associated milking unit 14, the associated filtration unit 14 and the effluent tube 30 are subjected to the appropriate negative pressure sufficient to accommodate removal of milk from the animal and the flow of milk from the engaged milking unit 14 into the storage tank 16.

With the lamp 54 of a given filtration unit 12 illuminated, a certain portion of the illumination will pass through the material of the filter 90 as milk flows therethrough and this will be detected by photoelectric cell 82. This will cause the gauge 86 to indicate normal opacity or transparency for the filter 90. When and if the filter 90 accumulates along its upper surface mastitis particles, the amount of illumination passing through the filter and being detected by the photoelectric cell 82 will decrease indicating at gauge 86 an abnormal reading. This reading may be used to sound an audio alarm, if desired. Alternatively, the valve 98 may be closed the housing 40 opened and the filter 90 visually examined to determine the presence or absence of mastitis particles and/or to determine whether or not a photoelectric cell 82 and the associated gauge 86 are working properly. If the housing 40 is substantially transparent, mastitis particles on the filter may be visually observed without opening the housing elements 40 and 42.

Accordingly, when mastitis particles are so detected, it is known exactly which animal is infected and allows for immediate segregation of the infected animal from the other animals of the herd together with prompt treatment of the infected animal to thereby avoid permanent mastitis damage to the udder of the infected animal while preventing the other animals of the herd from contracting the disease. The mastitis detection system according to the present invention is effective on a twice daily basis so that mastitis in a given animal is not permitted to remain for a protracted period of time without treatment. It is significant that the present invention accommodates retrofitting of existing vacuum milking systems by merely inserting a filtration unit within a vacuumized hose which accommodates flow of milk to the storage tank. The present system may be installed and utilized by persons having limited technical training and skill.

The invention may be embodied in other specific forms without departing from the spirit or essential characteristics thereof. The present embodiment is therefore considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A method of detecting mastitis in milk animals comprising the steps of continually filtering a stream of milk as it is derived from a given animal at a milking site prior to comingling the milk of said animal with the milk of another animal, collecting on a disposable filter at the filtering site clotted material, if any, indicating the existence of mastitis in said animal while entirely avoiding exposure of the milk of said animal to electrical conductivity, the mastitis accumulated on the filter at the filter site increasing the relative opacity of the filter, and optically detecting the presence and absence of mastitis on the filter at said filtering site so that the animal at each milking while at the milking site is known to be free of or in need of prompt treatment for mastitis.

2. A milking site mastitis detection system comprising:
   a milking machine system comprising vacuumized milk tank means, at least one teat-engaging milking means and hollow tube means by which the vacuum is communicated from the tank means to the milking means and by which milk derived from an animal at the milking means is communicated to the tank means;
   a mastitis detector disposed along and forming part of the flow path of the hollow tube means which avoids exposing the milk to electrical conductivity, the detector being located upstream of any comingling of milk from different animals, the mastitis detector being subject to the vacuum pressure of the milking machine system and comprising hollow housing means and milk filtering means within the housing means, the filtering means comprising a filter comprising material pervious to milk and impervious to mastitis particles wherein accumulation of mastitis particles on the filter at the filtering means increases the relative opacity thereof accommodating optical detection of said mastitis particles by examination of the filter at the filtering means as opposed to examination of the milk being displaced along the flow path, for instant identification of a specific infected animal, immediate segregation of the infected animal from the herd and prompt treatment of said animal thereby avoiding permanent mastitis damage to the udder of the infected animal and preventing other animals from contracting the disease.

3. A detection system according to claim 2 further comprising on/off valve means interposed between the mastitis detection and the milk tank means along the path of the vacuum so that when the valve is off, the interior of the mastitis detector is isolated from said vacuum.

4. A detection system according to claim 2 wherein the filtering means comprises a disposable replaceable filter element removably disposed within the housing means.

5. A detection system according to claim 2 wherein the housing means comprise shape retaining synthetic resinous material.

6. A detection system according to claim 2 wherein the housing means are substantially transparent.

7. A detection system according to claim 2 wherein the housing means comprise two hollow chambers separated by said filtering means, and one chamber comprising milk influent means and the other chamber comprising milk effluent means.

8. A detection system according to claim 7 wherein the two chambers are formed by oppositely directed essentially funnel shaped portions of said housing means.

9. A milking site mastitis detection system comprising:
a milking machine system comprising vacuumized milk tank means, at least one teat-engaging milking means and hollow tube means by which the vacuum is communicated from the tank means to the milking means and by which milk derived from an animal at the milking means is communicated to the tank means;
a mastitis detector which avoids exposing the milk to electrical conductivity interposed along the hollow tube means between the milking means and the tank means, upstream of any comingling of milk from different animals, the mastitis detector being subject to the vacuum pressure of the milking machine system and comprising hollow housing means and milk filtering means within the housing means, the filtering means comprising a material pervious to milk and impervious to mastitis particles wherein accumulation of mastitis particles at the filtering means increases the relative opacity thereof accommodating optical detection of said mastitis particles at the filtering means for instant identification of a specific infected animal, immediate segregation of the infected animal from the herd and prompt treatment of said animal thereby avoiding permanent mastitis damage to the udder of the infected animal and preventing other animals from contracting the disease;
the housing means comprising two hollow chambers separated by said filtering means, and one chamber comprising milk influent means and the other chamber comprising milk effluent means, milk overflow passageway means spanning between said two chambers remote from the filtering means to accommodate flow of milk when and if the filtering means becomes clogged.

10. A milking site mastitis detection system comprising;
a milking machine system comprising vacuumized milk tank means, at least one teat-engaging milking means and hollow tube means by which the vacuum is communicated from the tank means to the milking means and by which milk derived from an animal at the milking means is communicated to the tank means;
a mastitis detection which avoids exposing the milk to electrical conductivity interposed along the hollow tube means between the milking means and the tank means, upstream of any comingling of milk from different animals, the mastitis detector being subject to the vacuum pressure of the milking machine system and comprising hollow housing means and milk filtering means within the housing means, the filtering means comprising a material pervious to milk and impervious to mastitis particles wherein accumulation of mastitis particles at the filtering means increases the relative opacity thereof accommodating optical detection of said mastitis particles at the filtering means for instant identification of a specific infected animal, immediate segregation of the infected animal from the herd and prompt treatment of said animal thereby avoiding permanent mastitis damage to the udder of the infected animal and preventing other animals from contracting the disease;
light producing means disposed within the housing means on one side of the filtering means and light sensing means within the housing means on the other side of the filtering means for detecting changes in the relative opacity of the filtering means.

11. A detection system according to claim 10 wherein the housing means comprises at least two parts pivotably secured together by hinge means accommodating opening of one housing part relative to the other for visual inspection and to replace the filtering means.

12. A detection system according to claim 11 further comprising a compressable elastomeric vacuum seal interposed between the two housing parts.

13. A method of detecting mastitis in any one of several milk animals and simultaneously identifying the infected amimal comprising the steps of providing a separate filter site for each animal being milked at any point in time separately and continuously filtering the stream of milk as it is being derived from each animal at each of said filtering sites prior to comingling the milk of one animal with the milk of another animal, collecting at each filtering site clotted material, if any, indicating the existence of mastitis in the one animal being milked adjacent said filtering site while entirely avoiding exposure of the milk of any and all of the animals to electrical conductivity, the mastitis accumulated at any filtering site increasing the relative opacity of the filter at that site, and optically examining the opacity of each filter thereby detecting the presence and absence of mastitis on the filter at each filtering site so that each specific animal while at any said milking site is immediately known to be free of or in need of prompt treatment for mastitis.

14. A milking site mastitis detection system comprising:
a milking machine system comprising vaccumized milk tank means, a plurality of teat-engaging milking means and a plurality of hollow tube means by which the vacuum is communicated from the tank means to each milking means and by which milk derived from several animals at the plurality of milking means is communicated to the tank means;
a plurality of mastitis detectors one disposed along and forming part of the flow path of each hollow tube means which avoids exposing the milk to electrical conductivity, each detector being located upstream of any comingling of milk from different animals, each mastitis detector being subject to the vacuum pressure of the milking machine system and comprising hollow housing means and milk filtering means within the housing means, the filtering means comprising a disposable filter comprising material pervious to milk and impervious to mastitis particles wherein accumulation of mastitis particles on the filter at any filtering means increases the relative opacity thereof accommodating optical detection of said mastitis particles by examination of the filter at said filtering means as opposed to examination of the milk passing site, for instant identification of a specific infected animal, immediate segregation of the infected animal from the other animals and prompt treatment of said animal thereby avoiding permanent mastitis damage to the udder of the infected animal and preventing other animals from contracting the disease.

* * * * *